United States Patent [19]

Oeckl et al.

[11] Patent Number: 4,599,427
[45] Date of Patent: Jul. 8, 1986

[54] MICROBICIDAL AZOLYLMETHYLAMINES

[75] Inventors: Siegfried Oeckl, Bergisch-Gladbach; Hans-Georg Schmitt, Leverkusen; Wilfried Paulus; Hermann Genth, both of Krefeld, all of Fed. Rep. of Germany

[73] Assignee: Bayer Aktiengesellschaft, Leverkusen, Fed. Rep. of Germany

[21] Appl. No.: 536,929

[22] Filed: Sep. 28, 1983

[30] Foreign Application Priority Data

Oct. 13, 1982 [DE] Fed. Rep. of Germany ....... 3238006

[51] Int. Cl.$^4$ ................... A01N 43/50; A01N 43/653; A01N 43/80; C07D 249/08
[52] U.S. Cl. ...................................... 548/262; 544/59; 544/62; 544/132; 544/133; 544/139; 544/140; 544/366; 544/368; 544/370; 544/371; 546/198; 546/210; 546/211; 548/209; 548/263; 548/266; 548/336; 548/337; 548/339; 548/341; 548/342; 548/343; 548/374; 548/378
[58] Field of Search ................. 548/209, 262; 424/269

[56] References Cited

U.S. PATENT DOCUMENTS 4,350,702  9/1982  Baggaley ............................ 548/209

FOREIGN PATENT DOCUMENTS 357153   6/1980  Austria.
1004617  3/1957  Fed. Rep. of Germany.
631172   7/1982  Switzerland.
1113634  5/1968  United Kingdom ................ 548/209

OTHER PUBLICATIONS

Stocker et al, J. Org. Chem., vol. 35, pp. 883–887 (1970).

*Primary Examiner*—Alton D. Rollins
*Attorney, Agent, or Firm*—Sprung, Horn, Kramer & Woods

[57] ABSTRACT

The new azolylmethylamines can be prepared by reaction of amines and azoles with formaldehyde. They can be used in microbicidal agents.

1 Claim, No Drawings

MICROBICIDAL AZOLYLMETHYLAMINES

The invention relates to new azolylmethylamines, a process for their preparation and their use in microbicidal agents.

New azolylmethylamines have been found having the formula

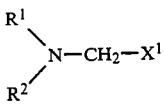
(I)

in which
$X^1$ denotes one of the radicals

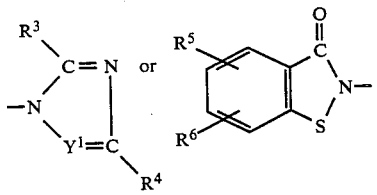

in which
$Y^1$ represents N or the group

and
$R^3$ to $R^7$ denote hydrogen, halogen, nitro, alkyl ($C_1$–$C_{24}$), cycloalkyl ($C_3$–$C_{12}$), alkoxy ($C_1$–$C_{24}$), cyano or aralkyl ($C_7$–$C_{24}$),
$R^1$ denotes alkyl ($C_1$–$C_{24}$), alkenyl ($C_2$–$C_{24}$), alkinyl ($C_2$–$C_{24}$), cycloalkyl ($C_3$–$C_{12}$), aralkyl ($C_7$–$C_{24}$), aminoalkyl ($C_1$–$C_{24}$), alkyleneaminoalkylene ($C_2$–$C_{24}$), aryl ($C_6$–$C_{18}$), alkylaryl ($C_7$–$C_{24}$), halogenoaryl ($C_6$–$C_{18}$), alkoxy ($C_1$–$C_{24}$), arylalkoxy ($C_7$–$C_{24}$) or the group $$-CH_2X^1$$

in which
$X^1$ has the abovementioned meaning,
$R^2$ denotes hydrogen or $R^1$,
$R^1$ having the abovementioned meaning, and it being possible for the radicals $R^1$ and $R^2$ to be linked in a heterocyclic 5-membered or 6-membered ring having one or more nitrogen, oxygen and/or sulphur or mixture thereof as heteroatoms.

According to the invention, halogen in this context can denote fluorine, chlorine, bromine or iodine, preferably fluorine and chlorine.

According to the invention, alkyl can denote a straight-chain or branched hydrocarbon radical having 1 to 24, preferably 1 to 18, carbon atoms. The following alkyl radicals may be mentioned as examples: methyl, ethyl, propyl, isopropyl, butyl, tert.-butyl, isoamyl, 2-ethylhexyl, octyl, dodecyl and stearyl.

According to the invention, alkenyl can denote a straight-chain or branched unsaturated hydrocarbon radical having 2 to 24, preferably 2 to 18, carbon atoms. In general, the alkenyl radicals contain one or two double bonds. The following alkenyl radicals may be mentioned as examples: propenyl, butenyl, hexenyl, octenyl, decenyl and dodecenyl.

According to the invention, alkinyl can denote a straight-chain or branched triply unsaturated hydrocarbon radical having 2 to 24, preferably 2 to 18, carbon atoms. In general, the alkinyl radicals contain one or two triple bonds. The following alkinyl radicals may be mentioned as examples: propinyl, butinyl, hexinyl, octinyl and dodecinyl.

According to the invention, cycloalkyl can denote a cyclic hydrocarbon radical having 3 to 12, preferably 5 to 7, carbon atoms. The following cycloalkyl radicals may be mentioned as examples: cyclopentyl, cyclohexyl, cycloheptyl and methylcyclohexyl.

According to the invention, alkoxy can denote a straight-chain or branched hydrocarbon radical which is bonded via oxygen and has 1 to 24, preferably 1 to 18, carbon atoms. The following alkoxy radicals may be mentioned as examples: methoxy, ethoxy, propoxy, isopropoxy, octyloxy, dodecyloxy, polyoxyethyleneoxy, aminoethyloxy and dimethylaminoethyloxy.

According to the invention, halogenoalkyl can denote a straight-chain or branched hydrocarbon radical which is substituted by halogen and has 1 to 24, preferably 1 to 18, carbon atoms. In this context, halogen can be fluorine, chlorine, bromine or iodine, preferably fluorine or chlorine. In general, the alkyl radicals can be substituted by one or more halogen atoms. However, it is also possible for the alkyl radicals to be perhalogenated. The following halogenoalkyl radicals may be mentioned as examples: chloroethyl, bromoethyl, dichloroethyl, trichloroethyl, chlorobutyl, chlorooctyl and chlorododecyl.

According to the invention, aralkyl can be a straight-chain or branched hydrocarbon radical which is substituted by aryl, preferably phenyl, naphthyl and biphenyl, and comprises a total of 7 to 24, preferably 7 to 12, carbon atoms. In general, the alkyl radicals are substituted by 1 to 2 aryl radicals.

According to the invention, aminoalkyl can denote a straight-chain or branched hydrocarbon radical which is substituted by amino groups and has 1 to 24, preferably 1 to 18, carbon atoms. In general, the aminoalkyl radicals are substituted by 1 to 10 amino groups. The following aminoalkyl radicals may be mentioned as examples: dimethylaminomethyl, diethylaminomethyl, dioctylaminomethyl, azolylaminomethyl, dimethylaminoethyl, dioctylaminoethyl and aminohexyl.

According to the invention, alkyleneaminoalkylene can be a polyamine in which, preferably, 2 to 100 lower alkylene groups (2 to 12 carbon atoms) are bonded together via amino groups of the formula

in which
$R^{15}$ denotes hydrogen or lower alkyl.
The following alkyleneaminoalkylene radicals may be mentioned as examples: ethyleneaminoethylene, diethylenediaminoethylene and triethylenetriaminoethylene.

According to the invention, aryl can be an aromatic radical having 6 to 18, preferably 6 to 12, carbon atoms. The following aryl radicals may be mentioned as examples: phenyl, naphthyl and biphenyl.

According to the invention, alkylaryl can be an aryl radical which is substituted by alkyl groups and has a total of 7 to 24, preferably 7 to 12, carbon atoms. In general, the aryl radicals, preferably phenyl, naphthyl and biphenyl, are substituted by 1 to 3 lower alkyl radicals (1 to, say, 8 carbon atoms). The following alkylaryl radicals may be mentioned as examples: benzyl, phenethyl and phenyloctyl.

According to the invention, halogenoaryl can be an aryl radical which is substituted by halogen and has 6 to 18, preferably 6 to 12, carbon atoms. Halogens which may be mentioned are fluorine, chlorine, bromine and iodine, preferably fluorine and chlorine. In general, the aryl radicals are substituted by 1 to 3 halogen atoms. However, it is also possible for the aryl radicals to be perhalogenated. The following halogenoalkyl radicals may be mentioned as examples: chlorophenyl, bromophenyl, iodophenyl, dichlorophenyl, trichlorophenyl, pentachlorophenyl and chloronaphthyl.

According to the invention, arylalkoxy can be a straight-chain or branched hydrocarbon radical which is substituted by aryl and bonded via oxygen and has a total of 7 to 24, preferably 7 to 12, carbon atoms. In this context, the alkoxy radical is generally substituted by one to 3 aryl radicals. The following arylalkoxy radicals may be mentioned as examples: benzyloxy, phenethoxy and phenyloctyloxy.

It is possible for the radicals $R^1$ and $R^2$ to be linked to form a heterocyclic 5-membered or 6-membered ring with nitrogen, oxyen and/or sulphur in the ring. In general, the ring contains 1 to 3, preferably 1 to 2, heteroatoms. The following heterocyclic radicals may be mentioned as examples: piperazinyl, methylpiperazinyl, morpholinyl, thiomorpholinyl, pyrrolidinyl, piperidinyl, hexamethyleneiminyl, indolinyl, 2-methylindolinyl and isoindolinyl.

According to the invention, azolylmethylamines of the formula

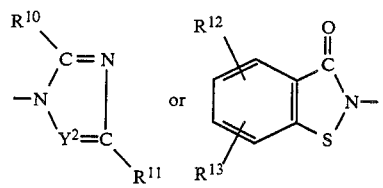
(II)

in which $X^2$ denotes one of the radicals

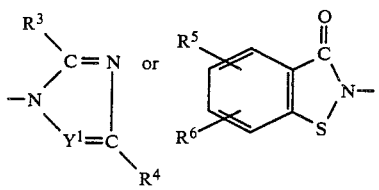

in which $Y^2$ represents N or the group

and $R^{10}$ to $R^{14}$ denote hydrogen, fluorine, chlorine, lower alkyl or lower alkoxy, $R^8$ denotes alkyl ($C_1$–$C_{18}$), alkenyl ($C_2$–$C_{18}$), cycloalkyl ($C_5$–$C_7$), aralkyl ($C_7$–$C_{12}$), aminoalkyl ($C_1$–$C_{18}$), alkyleneaminoalkylene, 2 to 100 lower alkylene groups being bonded together via amino groups of the formula

$R^{15}$ denotes hydrogen or lower alkyl, or $R^8$ denotes aryl ($C_6$–$C_{12}$), alkylaryl ($C_7$–$C_{12}$) halogenoaryl ($C_6$–$C_{12}$), alkoxy ($C_1$–$C_{18}$), arylalkoxy ($C_7$–$C_{12}$) or the group $-CH_2X^2$ in which $X^2$ has the abovementioned meaning,
$R^9$ denotes hydrogen or $R^8$, $R^8$ having the abovementioned meaning,
and it being possible for the radicals $R^8$ and $R^9$ to be linked to form a heterocyclic 5-membered or 6-membered ring having one or two nitrogen, oxygen and/or sulphur atoms or mixtures thereof as heteroatoms, are preferred.

The following azolylmethylamines may be mentioned as examples: 1,2,4-triazol-1-ylmethyldi-n-octylamine, bis-1,2,4-triazol-1-ylmethyl-n-dodecylamine, 2-(1-morpholinomethyl)-benzisothiazolin-3-one, 1-imidazolylmethyldi-n-octylamine and bis-1-imidazolylmethyl-n-dodecylamine.

In addition, a process for the preparation of the azolylmethylamines has been found, which is characterised in that azoles of the formula $HX^1$ (III)

in which $X^1$ denotes one of the radicals

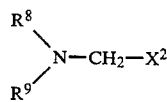

in which $Y^1$ represents nitrogen or the group

and
$R^3$ to $R^7$ denote hydrogen, halogen, nitro, alkyl ($C_1$–$C_{24}$), cycloalkyl ($C_3$–$C_{12}$), alkoxy ($C_1$–$C_{24}$), halogenoalkyl ($C_1$–$C_{24}$), cyano or aralkyl ($C_7$–$C_{24}$), are reacted with an amine of the formula

  (IV)

in which $R^1$ denotes alkyl ($C_1$–$C_{24}$), alkenyl ($C_2$–$C_{24}$), alkinyl ($C_2$–$C_{24}$), cycloalkyl ($C_3$–$C_{12}$), aralkyl ($C_7$–$C_{24}$), aminoalkyl ($C_1$–$C_{24}$), alkyleneaminoalkylene ($C_2$–$C_{24}$), aryl ($C_6$–$C_{18}$), alkylaryl ($C_7$–$C_{24}$), halogenoaryl ($C_6$–$C_{18}$), alkoxy ($C_1$–$C_{24}$), arylalkoxy ($C_7$–$C_{24}$) or the group $-CH_2X^1$ in which $X^1$ has the abovementioned meaning,
$R^2$ denotes hydrogen or $R^1$, $R^1$ having the abovementioned meaning, and it being possible for the radicals $R^1$ and $R^2$ to be linked to form a heterocyclic 5-membered or 6-membered ring with nitrogen, oxygen and/or sulphur as heteroatoms, and with formaldehyde at an elevated temperature, optionally in the presence of a solvent.

The process according to the invention can be illustrated, for example, by means of the following equation:

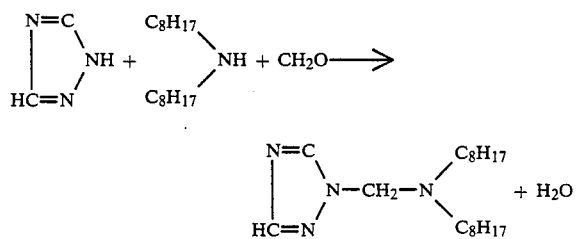

The azoles for the process according to the invention can be represented by the formulae

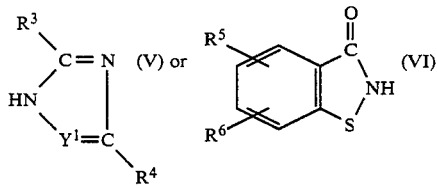

in which $R^3$ to $R^6$ have the abovementioned meaning. The azoles for the process according to the invention are known per se (Angew. Chemie 71, 753 (1959); Chem. Reviews 61, 87 (1961)).

The following azoles may be mentioned as examples: pyrazole, imidazole, 1,2,4-triazole, benzo[1,2]isothiazolin-3-one, 2-methylimidazole, 2-methyl-4-nitroimidazole and 2-methyl-5-nitroimidazole, tribromoimidazole, triiodoimidazole, dibromotriazole, diiodotriazole, chlorobenzisothiazolinone, dichlorobenzisothiazolinone, methylbenzisothiazolinone and nitrobenzisothiazolinone.

Amines for the process according to the invention are known per se and can be prepared by known processes.

The formaldehyde for the process according to the invention is generally employed as paraformaldehyde or as a solution of formaldehyde in water.

The process according to the invention is generally carried out at an elevated temperature, preferably in the temperature range from 0° to 100° C., in particular in the temperature range from 30° to 40° C.

In general, the process according to the invention is carried out under normal pressure. However, it is also possible to carry out the process according to the invention under subatmospheric or superatmospheric pressure, for example in the pressure range from 0.5 to 10 bar.

The process according to the invention can be carried out with or without a solvent. In general, solvents are used which do not change under the reaction conditions according to the invention. Examples of solvents which may be mentioned are aprotic solvents, such as dichloromethane, dichloroethane, trichloroethane, trichloroethylene, tetrachloroethylene, benzene, toluene, chlorobenzene, chlorotoluenes and diethyl ether.

In general, the process according to the invention is carried out as follows:

The amine and the azole are initially introduced with or without a solvent, and the formaldehyde is added. The reaction takes place exothermically with water being split off. The water of reaction can be removed by customary methods, for example by applying a vacuum, addition of drying agents or azeotropic distillation.

In a preferred embodiment of the process according to the invention, the amine and the azole are initially introduced in an inert solvent, and the aqueous formaldehyde solution is metered in. The temperature rises and is maintained in the temperature range according to the invention by cooling. A water-binding agent is added even before, or after, the reaction has finished, and stirring is continued in the temperature range according to the invention.

The course and the completion of the reaction can be checked using spectroscopic methods (NMR or IR). After reaction is complete, the solid material is filtered off and the solution is evaporated.

The azolylmethylamines according to the invention can be used as active compounds for controlling microorganisms, in particular in industrial materials which can be damaged by microorganisms.

According to the invention, industrial materials are non-living materials which have been produced for use in industry. Examples of industrial materials which are to be protected by active compounds according to the invention from microbial alteration or damage can be adhesives, glues, papers and cardboards, textiles, leather, wood, coating agents, plastic articles, cooling lubricants and other materials which can be decomposed by microorganisms. Within the scope of materials to be protected, there may be mentioned parts of production plants, for example cooling water circulations, which can be adversely affected by microorganisms. Industrial materials within the scope of the present invention which may preferably be mentioned are adhesives, glues, papers, cardboards, leather, wood, coating agents, cooling lubricants and cooling circulations.

Examples of microorganisms which can bring about degradation or alteration of the industrial materials are bacteria, fungi, yeasts, algae and slime organisms. The substances according to the invention preferentially act against bacteria, moulds, in particular fungi with discolour and damage wood (Basidiomycetes), and against slime organisms and algae.

Examples of microorganisms which may be mentioned are those of the following genera:
Alternaria, such as *Alternaria tenuis*, Aspergillus, such as *Aspergillus niger*, Chaetomium, such as *Chaetomium globosum*, Coniophora, such as *Coniophora cerebella*, Lentinus, such as *Lentinus tigrinus*, Penicillium, such as *Penicillium glaucum*, Polyporus, such as *Polyporus versicolor*, Aureobasidium, such as *Aureobasidium pullulans*, Sclerophoma, such as *Sclerophoma pityophila*, Staphylococcus, such as *Staphylococcus aureus*, Pseudomonas, such as *Pseudomonas aeruginosa*, Escherichia, such as *Escherichia coli*, and also green, blue and brown algae and diatoms.

Depending on the area of applicaion, the active compounds according to the invention can be converted into the customary formulations, such as solutions, emulsions, suspensions, powders, pastes and granules. These can be prepared in a manner known per se, for example, by mixing the active compounds with a diluent which consists of a liquid solvent and/or solid vehicles, optionally using surface-active agents, such as emulsifiers and/or dispersing agents, and in the case where, for example, water extenders are used, organic solvents, such as alcohols, can be used as auxiliary solvents if necessary.

Organic solvents for the active compounds can be, for example, alcohols, such as lower aliphatic alcohols, preferably ethanol or isopropanol, or benzyl alcohol, ketones, such as acetone or methyl ethyl ketone, liquid hydrocarbons, such as petroleum fractions, or chlorinated hydrocarbons, such as 1,2-dichloroethane.

The concentration in which the active compounds according to the invention are used depends on the type and occurrence of the microorganisms which are to be controlled, as well as on the composition of the material to be protected. The optimum amount to be employed can be found using test series. Generally, the concentration for use is in the range from 0.001 to 5% by weight, preferably from 0.01 to 0.5% by weight, relative to the material to be protected.

The novel active compounds according to the invention can also be in the form of a mixture with other known active compounds. The following active compounds may be mentioned as examples: benzyl alcohol mono(poly)hemiformal, benzimidazolylmethyl carbamate, tetramethylthiuram disulphide, zinc salts of dialkyl thiocarbamates, 2,4,5,6-tetrachloroisophthalonitrile, thiazolylbenzimidazole, mercaptobenzothiazole and phenol derivatives, such as 2-phenylphenol, (2,2'-dihydroxy-5,5'-dichloro)diphenylmethane and 3-methyl-4-chlorophenol.

(A) PREPARATION EXAMPLES

EXAMPLE 1

1,2,4-Triazol-1-ylmethyldi-n-octylamine 77 g (0.77 mol) of 30% strength formaldehyde solution were added dropwise to 187 g (0.77 mol) of di-n-octylamine and 54 g (0.77 mol) of 1,2,4-triazole in 400 ml of methylene chloride (or ethylene chloride) at such a rate that the temperature rose to 30° to 35° C. After addition of 200 g of anhydrous sodium sulphate, the mixture was stirred at 35° to 40° C. for 10 to 20 hours, the suspension was filtered off and the filtrate was evaporated. Yield 244 g (98%) of a clear pale yellow oil, $n_D^{20}$: 1.4709.

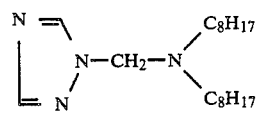

EXAMPLE 2

Bis-1,2,4-triazol-1-ylmethyl-n-dodecylamine 40 g (0.4 mol) of 30% strength aqueous formaldehyde solution were added dropwise to a mixture of 37 g (0.2 mol) of n-dodecylamine, 28 g (0.4 mol) of 1,2,4-triazole and 300 g of anhydrous sodium sulphate in 360 ml of methylene chloride at such a rate that a temperature of 40° C. was reached. The mixture was then stirred at 40° C. for 5 hours, filtered and the filtrate was evaporated. 62.5 g (90%) of a white wax-like material which did not have a sharp melting point were obtained. The structure was confirmed by the NMR spectrum.

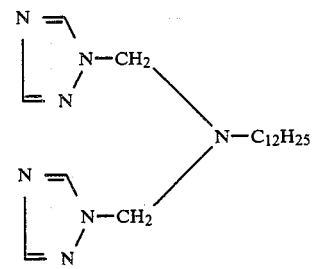

EXAMPLE 3

2-(1-Morpholinomethyl)benzisothiazolin-3-one 15.1 g (0.1 mol) of benzisothiazolin-3-one were suspended in 100 ml of methylene chloride. 8.7 g (0.1 mol) of morpholine were added at room temperature. The benzisothiazolin-3-one dissolved during this. 10 g (0.1 mol) of 30% strength formalin solution were added dropwise and the mixture was then stirred at 30° to 32° C. for 6 hours.

Sodium sulphate was added until the methylene chloride solution was clear. After filtration, the solvent was removed in vacuo in a rotary evaporator at temperatures below 35° C. The oil remaining crystallised after brief standing: 24 g (96% of theory), colourless crystals, melting point 61°–63° C.

Elemental analysis: Calculated C 57.58; H 5.64; N 11.19. Found: C 57.5; H 5.7; N 11.1.

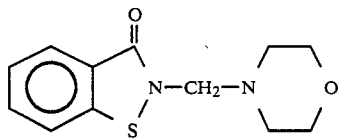

EXAMPLES 4 TO 82

The other azolylmethylamines were prepared in accordance with Example 1:

| Example No. | Structure | Yield in % | Refractive index ($n_D^{20}$) or melting point (°C.) |
|---|---|---|---|
| 4 | A—N(morpholine) | 80 | 80–83° C. |
| 5 | B—N(morpholine) | 100 | 73° C. |
| 6 | C—N(morpholine) | 100 | 66° C. |
| 7 | A—N(dicyclohexyl) | 96 | 76° C. |
| 8 | B—N(dicyclohexyl) | 93 | 68° C. |

-continued
| | | | |
|---|---|---|---|
| 9 | 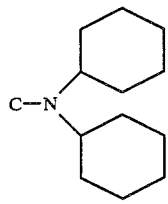 | 85 | 40° C. |
| 10 | 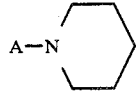 | 98 | 62° C. |
| 11 | 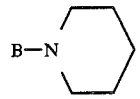 | 96 | 1.5181 |
| 12 | 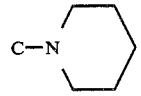 | 100 | 1.5100 |
| 13 | 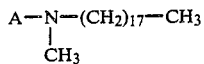 | 86 | 60° C. |
| 14 | 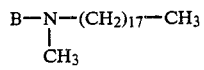 | 88 | 63° C. |
| 15 | 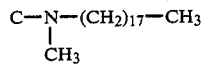 | 93 | 38° C. |
| 16 | 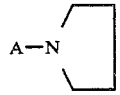 | 96 | 1.5060 |
| 17 | 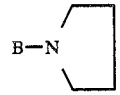 | 96 | 1.5168 |
| 18 | A—N(CH$_3$)$_2$ | 68 | 1.4800 |
| 19 | B—N(CH$_3$)$_2$ | 66 | 1.4959 |
| 20 | C—N(CH$_3$)$_2$ | 96 | 1.4832 |
| 21 | A—N(C$_2$H$_5$)$_2$ | 95 | 1.4783 |
| 22 | B—N(C$_2$H$_5$)$_2$ | 90 | 1.4910 |
| 23 | C—N(C$_2$H$_5$)$_2$ | 98 | 1.4791 |
| 24 | 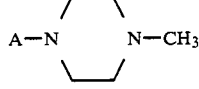 | 89 | 75° C. |
| 25 | 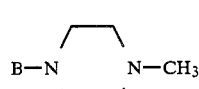 | 92 | 77° C. |
| 26 | 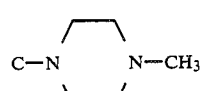 | 95 | 32° C. |

-continued
| | | | |
|---|---|---|---|
| 27 | 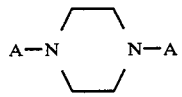 | 70 | 206° C. |
| 28 | 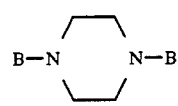 | 31 | 174° C. |
| 29 | 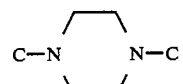 | 100 | 107° C. |
| 30 | 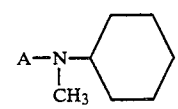 | 100 | 1.5062 |
| 31 | 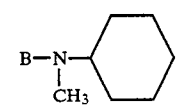 | 100 | 1.5137 |
| 32 | 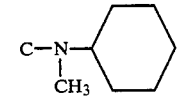 | 95 | 1.5064 |
| 33 | 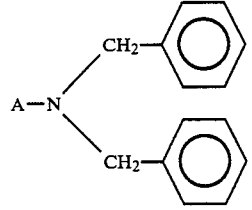 | 94 | 64° C. |
| 34 | 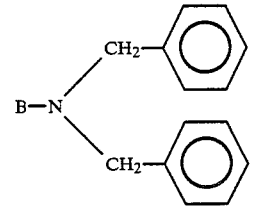 | 100 | 63° C. |
| 35 | 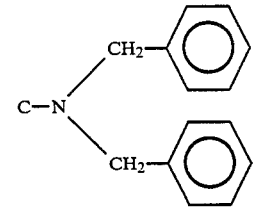 | 95 | 44° C. |
| 36 | 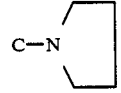 | 99 | 1.5075 |
| 37 | 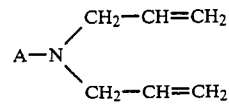 | 97 | 1.4985 |

-continued

| | | | |
|---|---|---|---|
| 38 | B—N(CH₂—CH=CH₂)₂ | 91 | 1.5090 |
| 39 | C—N(CH₂—CH=CH₂)₂ | 98 | 1.4972 |
| 40 | B—N(C₈H₁₇)₂ | 81 | 1.4764 |
| 41 | C—N(C₈H₁₇)₂ | 73 | 1.4712 |
| 42 | A—N(—CH₂—CH(C₂H₅)—C₄H₉)₂ | 95 | 1.4721 |
| 43 | B—N(—CH₂—CH(C₂H₅)—C₄H₉)₂ | 83 | 1.4788 |
| 44 | C—N(—CH₂—CH(C₂H₅)—C₄H₉)₂ | 97 | 1.4728 |
| 45 | A—NH—C₁₂H₂₅ | 86 | 51° C. |
| 46 | A₂N—cyclohexyl | 46 | very viscous |
| 47 | A—N(CH₃)—CH₂—CH₂—N(CH₃)—CH₂—CH₂—N(CH₃)—A | 78 | 1.5161 |
| 48 | B—N(CH₃)—CH₂—CH₂—N(CH₃)—CH₂—CH₂—N(CH₃)—B | 70 | 1.5296 |
| 49 | C—N(CH₃)—CH₂—CH₂—N(CH₃)—CH₂—CH₂—N(CH₃)—C | 85 | 1.5195 |
| 50 | A—N(azepane) | 98 | 1.5120 |
| 51 | A—N(azepane) | 95 | 37° C. |
| 52 | 2-methyl-1-A-indoline | 85 | — |

| | | | |
|---|---|---|---|
| 53 | 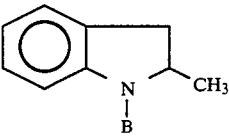 | 88 | — |
| 54 | 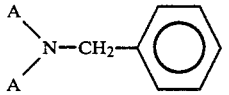 | 97 | 1.5566 |
| 55 | 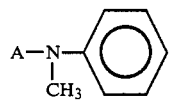 | 94 | 1.5847 |
| 56 | 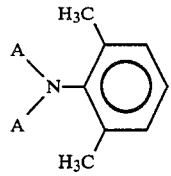 | 77 | 1.5590 |
| 57 | 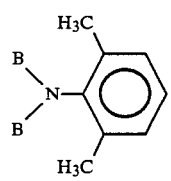 | 100 | 1.5605 |
| 58 | 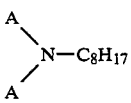 | 93 | 1.4922 |
| 59 | 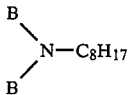 | 100 | 1.5031 |
| 60 | 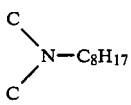 | 100 | 1.4958 |
| 61 | 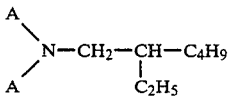 | 98 | 1.4949 |
| 62 | 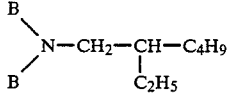 | 100 | 1.5035 |
| 63 | 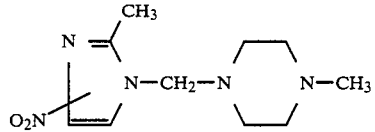 | 95 | 77° C. |
| 64 | 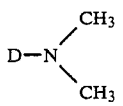 | 91,3 | 83–6° C. |

| | | | |
|---|---|---|---|
| 65 | 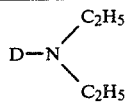 D—N(C₂H₅)₂ | 89,0 | 41–2° C. |
| 66 | 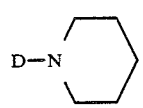 D—N(piperidine) | 86,7 | 88–91° C. |
| 67 | 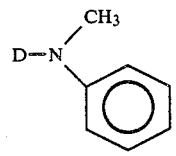 D—N(CH₃)(C₆H₅) | 92,6 | 96–8° C. |
| 68 | 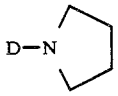 D—N(pyrrolidine) | 81,2 | 79–80° C. |
| 69 | 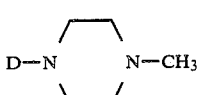 D—N(N-methylpiperazine) | 91,2 | 102–3° C. |
| 70 | 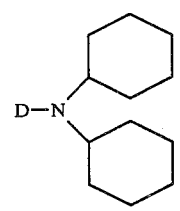 D—N(cyclohexyl)₂ | 81,9 | 93–4° C. |
| 71 | 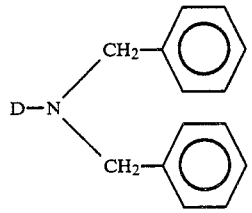 D—N(CH₂C₆H₅)₂ | 83,3 | 62–4° C. |
| 72 | 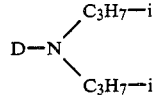 D—N(i-C₃H₇)₂ | 83,2 | 62° C. |
| 73 | 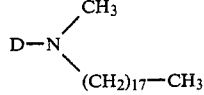 D—N(CH₃)((CH₂)₁₇CH₃) | 82,9 | 63° C. |
| 74 | 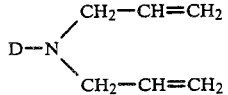 D—N(CH₂—CH=CH₂)₂ | 84,6 | 1.5961 |
| 75 | 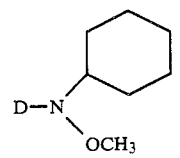 D—N(cyclohexyl)(OCH₃) | 77,0 | 89–91° C. |

| | | | |
|---|---|---|---|
| 76 | 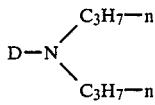 | 89,0 | 1.5712 |
| 77 | 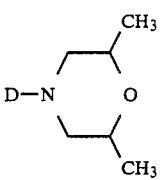 | 93,5 | 1.5738 |
| 78 | 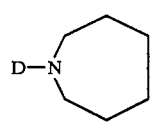 | 87,8 | 64–7° C. |
| 79 | 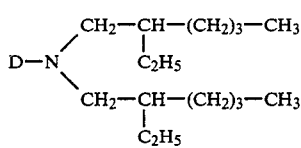 | 80,4 | 1.5288 |
| 80 | 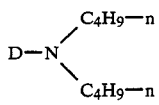 | 87 | 43–5° C. |
| 81 | 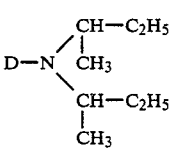 | 94,2 | 46–8° C. |
| 82 | 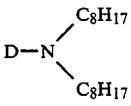 | 93,9 | 1.5288 |
| 83 | 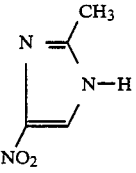 | Comparison Example | |

(B) USE EXAMPLES

EXAMPLE 83

In order to demonstrate the effectiveness against fungi, the minimum inhibitory concentrations (MIC) of active compounds according to the invention were determined:

Active compounds according to the invention were added, at concentrations from 0.1 mg/liter to 5,000 mg/liter, to an agar prepared from beerwort and peptone. After the agar had solidified, it was contaminated with pure cultures of the test organisms listed in the table. The MIC was determined after storage at 28° C. and 60 to 70% relative atmospheric humidity for 2 weeks. The MIC is the lowest concentration of active compound at which the microbial species used shows no growth at all, and it is reported in the table below.

TABLE I

Report of the MIC values in mg/l for the action of substances according to the invention of fungi

| Test organisms | MIC (in mg/l) of active compound according to the Examples: | | | | | | | | | | | | | | | |
|---|---|---|---|---|---|---|---|---|---|---|---|---|---|---|---|---|
| | 1 | 2 | 3 | 40 | 41 | 42 | 43 | 44 | 45 | 59 | 64 | 65 | 66 | 68 | 69 | 70 |
| *Alternaria tenuis* | 50 | | | 50 | 50 | | | | | | | | 35 | | | 150 |
| *Aspergillus niger* | 100 | 350 | 150 | 200 | 200 | 500 | 500 | 500 | 500 | 500 | 350 | 150 | 350 | 100 | 200 | 350 |
| *Aureobasidium pullulans* | 50 | | | 15 | 35 | | | | | | | | 20 | | | 50 |
| *Chaetomium globosum* | 200 | 200 | 200 | 75 | 75 | 200 | 150 | 200 | 150 | 500 | 150 | 100 | 200 | 200 | 350 | 200 |

TABLE I-continued

Report of the MIC values in mg/l for the action of substances according to the invention of fungi

| | MIC (in mg/l) of active compound according to the Examples: | | | | | | | | | | | | | | | |
|---|---|---|---|---|---|---|---|---|---|---|---|---|---|---|---|---|
| Coniophora cerebella | 20 | | | 10 | 10 | | | | | | | 75 | | | 20 |
| Lentinus tigrinus | 20 | | | 20 | 20 | | | | | | | 100 | | | 50 |
| Penicillium glaucum | 50 | 200 | 75 | 50 | 50 | 500 | 200 | 500 | 200 | 500 | 150 | 200 | 150 | 150 | 75 | 150 |
| Polyporus versicolor | 100 | | | 50 | 50 | | | | | | | 50 | | | 50 |
| Sclerophoma pityophila | 20 | | | 20 | 20 | | | | | | | 50 | | | 50 |
| Trichoderma viride | 200 | | | 100 | 150 | | | | | | | 200 | | | 200 |

| Test organisms | 67 | 71 | 72 | 73 | 74 | 75 | 76 | 77 | 78 | 80 | 82 | 87 |
|---|---|---|---|---|---|---|---|---|---|---|---|---|
| Aspergillus niger | 350 | 200 | 200 | 500 | 200 | 200 | 150 | 200 | 200 | 200 | 100 | >1000 |
| Chaetomium globosum | 200 | 350 | 200 | 200 | 200 | 100 | 200 | 200 | 350 | 200 | 50 | >1000 |
| Pencillium glaucum | 350 | 200 | 200 | 200 | 200 | 100 | 100 | 100 | 350 | 100 | 50 | >1000 |

EXAMPLE 84

Action against bacteria

Active compounds according to the invention are added, at concentrations from 1 to 5,000 ppm, to an agar which contains broth as nutrient medium. The nutrient medium is then infected with the particular test organisms listed in Table II and the infected medium is kept at 28° C. and 60 to 70% relative atmospheric humidity for 2 weeks. The MIC is the lowest concentration of active compound at which the microbial species used shows no growth at all. The MIC values are given in Table II.

TABLE II

Report of the MIC values in mg/l for the action on bacteria of the active compounds indicated below.

| | MIC (in mg/l) of active compound according to the Examples: | | | | | | | |
|---|---|---|---|---|---|---|---|---|
| Test Organisms | 1 | 2 3 40 | 45 | 64 | 79 | 81 | | 87 |
| Escherichia coli | 75 | 50 50 50 | 50 | <20 | 50 | 50 | | >1000 |
| Staphylococcus aureus | <20 | <20 35 5 | <20 | <20 | <20 | 50 | | >1000 |
| Pseudomonas aeruginosa | 750 | | | | | | | |
| Pseudomonas fluorescens | 750 | | | | | | | |
| Bacillus subtilis | 5 | | | | | | | |
| Bacterium punctatum | 20 | | | | | | | |
| Proteus vulgaris | 100 | | | | | | | |
| Leuconostoc mesenteroides | 20 | | | | | | | |

EXAMPLE 85

(Action against slime organisms)

Substances according to the invention, dissolved in a little acetone, are used in concentrations of 0.1 to 100 mg/liter in each case in Allen's nutrient solution (Arch. Microbiol. 17, 34 to 53 (1952)), which contains 0.2 g of ammonium chloride, 4.0 g of sodium nitrate, 1.0 g of dipotassium hydrogen phosphate, 0.2 g of calcium chloride, 2.05 g of magnesium sulphate, 0.02 g of iron chloride and 1% caprolactam in 4 liters of sterile water. The nutrient solution is infected with slime organisms (about $10^6$ organisms/ml), which have been isolated from spinning water cycles used in polyamide manufacture, shortly beforehand. Nutrient solutions which contain the minimum inhibitory concentration (MIC) or higher concentrations of active compound are still completely clear after culturing at room temperature for 3 weeks, that is to say, the great increase in microbes and formation of slime which is noticeable after 3 to 4 days in nutrient solutions not containing active compound does not occur.

TABLE III

MIC values in mg/liter for the action on slime organisms of the substances indicated below.

| Active compound according to Example | MIC in mg/l |
|---|---|
| 1 | 75 |
| 2 | 20 |
| 3 | 5 |
| 40 | 30 |
| 45 | 20 |
| 66 | 3 |
| 68 | 5 |
| 70 | 5 |
| 82 | 3 |

EXAMPLE 86

A mixed culture of green, blue and brown algae and diatoms (*Stichococcus bacillaris* Naegeli, *Euglena gracilis* Klebs, *Chlorella pyronoidosa* Chick, *Phormidium foveolarum* Gomont, *Oscillatoria geminata* Meneghini and *Phaedodactylum tricornutum* Bohlin) is added, while bubbling air through, to Allen's nutrient solution (Arch. Microbiol. 17, 34 to 53 (1952)), which contains 0.2 g of ammonium chloride, 4.0 g of sodium nitrate, 1.0 g of dipotassium hydrogen phosphate, 0.2 g of calcium chloride, 2.05 g of magnesium sulphate and 0.02 g of iron chloride in 4 liters of sterile water. After 2 weeks, the nutrient solution is coloured a deep greenish blue due to intensive growth of algae. The death of the algae after addition of active compounds according to the invention is seen by the decolorisation of the nutrient solution.

TABLE IV

Algicidal concentrations (mg/liter) of the substances indicated below

| Active compound according to Example | Algicidal concentration in mg/liter |
|---|---|
| 1 | 20 |

| Active compound according to Example | Algicidal concentration in mg/liter |
| --- | --- |
| 2 | 75 |
| 3 | 100 |
| 40 | 20 |
| 41 | 15 |
| 45 | 75 |
| 68 | 100 |
| 70 | 100 |
| 82 | 20 |
What is claimed is:
1. An azolylmethylamine of the formula
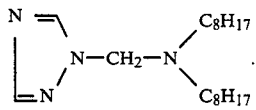
* * * * *